US006139149A

United States Patent [19]

Shafer et al.

[11] Patent Number: 6,139,149

[45] Date of Patent: Oct. 31, 2000

[54] DEVICE TO REDUCE EYE STRAIN

[75] Inventors: Marvin Lyle Shafer, 1056 W. Wellington, Chicago, Ill. 60657; Michelle Carol Shafer, Chicago, Ill.

[73] Assignee: Marvin Lyle Shafer, Chicago, Ill.

[21] Appl. No.: 09/432,236

[22] Filed: Nov. 3, 1999

[51] Int. Cl.[7] .......... A61B 3/00

[52] U.S. Cl. .......... 351/203

[58] Field of Search .......... 351/203, 200, 351/245, 246

[56] References Cited

U.S. PATENT DOCUMENTS

| | | | |
|---|---|---|---|
| 1,464,075 | 8/1923 | Hull | 351/203 |
| 3,698,800 | 10/1972 | Belgau | 351/203 |
| 4,932,457 | 6/1990 | Duncan . | |
| 5,141,046 | 8/1992 | Duncan . | |
| 5,880,811 | 3/1999 | Parisi | 351/203 |

*Primary Examiner*—George Manuel

[57] ABSTRACT

The invention is a method of using a moving, three-dimensional air sculpture which, when used in close proximity, by the fact that it is attached directly, to a computer monitor or a video display terminal, will relieve eye strain resulting from fixed plane focus. In this way the computer operator can pleasurably reverse the symptoms of eye fatigue and stress by viewing the invention and inadvertently engage in an eye exercise program.

11 Claims, 7 Drawing Sheets

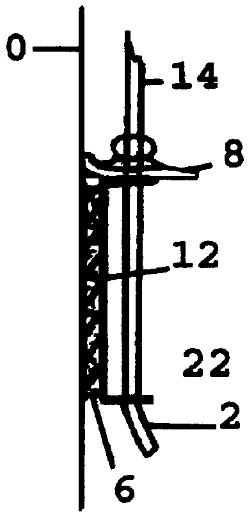
Profile View Fig. 2
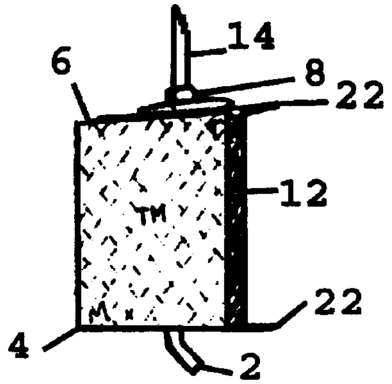
3/4 Back side View Fig. 3
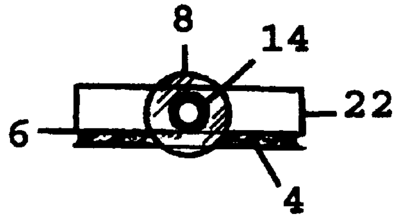
Top View Fig. 4

DEVICE TO REDUCE EYE STRAIN

CROSS-REFERENCE TO RELATED APPLICATIONS Not Applicable

STATEMENT REGARDING FEDERALLY SPONSORED RESEARCH OR DEVELOPMENT Not Applicable

REFERENCE TO A MICROFICHE APPENDIX Not Applicable

BACKGROUND OF THE INVENTION

Daily use of computers at the workplace, in educational institutions, and in the home cause many people to spend long hours in intense visual concentration directed at computer monitors or related instruments that present a flat focal plane. Since, such monitors and related instruments require the eyes to remain at a fixed focus distance for long periods, such activity may thereby cause eye strain and fatigue, weakening of the eye muscles, and the gradual limitation or loss of visual function with prolonged use. The vision risks associated with using computer monitors and video display terminals (VDTs) has been described by OSHA in an extensive study release May, 1989. Major publications such as U.S. News and World Report, Forbes, Scientific American, PC Personal Computing, and PC Week have repeatedly discussed growing problems with eye strain in the workplace that are associated with prolonged use of computers. Eye patients who suffer visual strain and fatigue are often prescribed daily eye exercises which usually involve the repeated movement of common objects such as two pencils back and forth in front of the eyes thereby changing the focal plane and exercising a variety of eye functions.

United States Patents have been awarded for several inventions that are used in conjunction with computer monitors or VDTs that are intended to provide such eye exercises and or to relieve eye strain associated with extended use.In related art, U.S. Pat. No. 5,204,702 describes a modified lens method for relieving eye strain and fatigue associated with extended viewing of VDTs. Separately, U.S. Pat. No. 5,200,859 describes an adjustable mirror system that also is designed to save vision and reduce eye strain and focusing problems associated with viewing computer monitors or VDTs. Separately, Bonham (U.S. Pat. No. 5,040,888) describes a hologram system which helps reduce eye strain and focusing problems associated with extended use of computer monitors or VDTs by presenting alternating or shifting holographic images which appear to be focused at different planes and thus cause exercise of the ciliary muscle of the eye. This device requires intentional physical movement of the user and or a motorized and illuminating device with timing mechanisms. All of the above inventions are relatively expensive and require specific adaptations and actions by the user.

Applicants have devised small and inexpensive simple mechanical devices, which can relieve or prevent eye strain or other visual dysfunction by being placed besides or on top of a computer monitor or similar instruments during the working period. These devices are comprised of one or more wire-like structural elements, one or more flexible connectors, and one or more light weight visual elements of variable size, color or shape that provide visual interest or entertainment. The structural elements are devised to hold the device or to carry the visual elements, and the connectors are designed to allow free and easy motion of one or more structural element and one or more visual element.

Consequently, when the parts are designed and put together in a balanced configuration, said device or individual parts thereof will rotate and move in a somewhat random manner due to the motion of ambient air and without requiring mechanical or electrical forces to intentionally move the device. In that sense the device is self-powered once installed on or near the monitor. Since the visual elements and other parts will randomly move back and forth as well as laterally in the focal plane, involuntary as well as voluntary attention to the device will thereby exercise the eyes, relieve eye strain, and prevent vision dysfunction. This device has considerable advantages in terms of low cost, ease of use, easy acceptance and ease of replacement.

The invention is designed to appear decorative and entertaining, akin to the large sculptures made famous by the late Alexander Calder and similar to the artistic mobile sculptures designed, made and marketed by the Applicants for home and corporate art display. However, when manufactured in miniature form and displayed within approximately one foot of the viewing area of the computer monitor, it serves a different medical health function as described herein—even if the user is unaware of this function. Consequently, the invention can be provided in the workplace by the owners or officers of a company in order to reduce and alleviate eye strain as a medical health measure—even though the employees thereof may not be aware of the health effects, even if they may not intentionally use these devices for said health effects, and even if they commonly regard the invention as a decorative, entertaining or tasteful object of art. Since the health value of eye exercise is well known, employers may thereby receive some consideration or discount from their medical insurance company for providing and using said invention in the workplace, and thus there is a potential economic benefit as well as a potential health benefit to the use of such devices.

Since the medical health value of the invention is expected to gradually diminish over time as habituation ensues from repeated and or prolonged exposure, there is a need to remove and replace specific devices over time with other devices that provide different visual experiences and eye exercises as needed. Applicants have therefore devised modular connectors and related methods to easily and inexpensively create multiple embodiments of the invention with different structural, visual and motive characteristics. Consequently, said modular design is an important feature of the basic invention since the medical health value of the device is maintained or renewed by the repeated replacement by alternate embodiments of the same invention. The economic value of the invention is therefore dependent on patent protection for all alternate embodiments which employ this basic design of providing small mobile devices of visual interest that move somewhat randomly in the focal plane and that are attached to or in the near vicinity of computer monitors or other flat plane instruments.

BRIEF SUMMARY OF THE INVENTION

The invention disclosed herein includes methods and compositions for the manufacture of a non-invasive medical health device. Said mechanical device consists of small structural elements of a linear or wire-like nature, visual attention-getting elements composed of light weight objects of colorful, enticing or beautiful design, and simple modular connectors that allow easy motion or rotation of all or part of the structural and visual elements, all of which are balanced and conjoined together so that the parts will move somewhat randomly with the forces of ambient air. The employment of this invention on the top of or near to a computer monitor or other fixed focus instrument provides involuntary and voluntary visual exercise for the eyes by rotating and moving objects of visual interest unpredictably in the visual plane including motion backward and forward. Such exercise is known to relieve eye strain and to exercise the eye muscles and may ameliorate or prevent visual dysfunction that might result from repeated use of computer monitors and similar instruments.

The basic invention includes modular design elements that allow the easy manufacture of a variety of alternate embodiments of similar medical health value. The repeated substitution of one embodyment of the invention with alternate embodiments is also part of the basic invention since individuals habituate to repeated exposure to the same or similar stimuli. Therefore, variant and future alternate compositions and methods of the inventors subject matter are hereby included within the scope of the present invention.

BRIEF DESCRIPTION OF THE SEVERAL VIEWS OF THE DRAWING

The enclosed drawings represent an application of the invention. The embodyment shown in the drawings functions to relieve eyestrain thru encouraging eye exercise by the viewer.

DETAILED DESCRIPTION OF THE INVENTION

Figure 1:
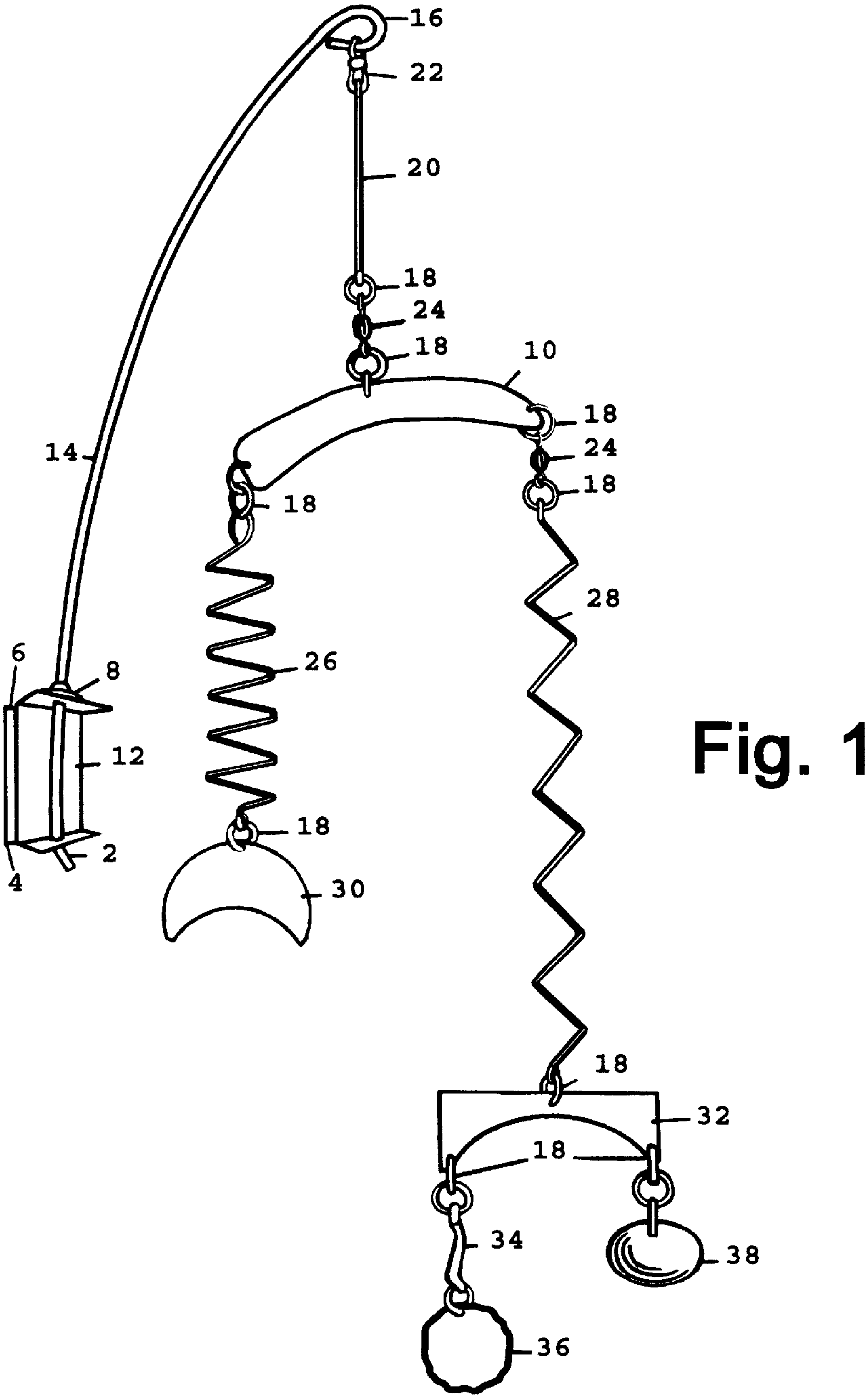

FIG. 1 is a perspective view of the preferred embodyment of the invention. A method for relieving eye strain resulting from extended use of a computer monitor by an operator, the method utilizing a means capable of changing its structural orientation to present a variable appearance, said variable appearance means having a supporting rod (#14) with two ends. The first end (bent to deter theft #2) having associated attachment means capable for a connection (back of aluminum C-shaped bracket #12) (double stick tape #6) (backing on double stick tape # 4) to a flat surface of a computer monitor (#0) and the second end (rod loop #16) having rotationally suspended visual elements (spring clip for changing embodiments of the invention #22). The method comprising the steps of connecting the attachment means to a monitor in a location visible to the operator (rubber washer #8 to hold connecting rod #14 in place by the traction of the edge of the washer engaging the side of the monitor) where the visual elements (textured balancing element #10, wireform #26 hanging from 1st end of #10, wireform #28 hanging from 2nd end of #10, distal visual unit #30, distal balancing unit #32, distal unit #38 hanging from 1st end of balancing element #32, wireform #34 hanging from 2nd end of distal balancing element #32, and textured distal unit #36) are free to move rotationally (jump rings #18, spinners #24 and wireform #20) and periodically focusing the eyes of the operator on the mobile visual elements.

FIG. 2, FIG. 3 and FIG. 4 are is three perspective, detailed views of the bracket (#12)and a portion of the connecting arm (#14) of the preferred embodiment. FIG. 2, a profile, shows the clear rubber washer (#8) engaged to the monitor chassis, stabilizing the connecting rod (#14). FIG. 3, the back of this bracket has a piece of double-stik tape (#6) affixed to it. The backing on this tape (#4) is removed to adhere the mobile to the monitor. FIG. 4 shows Rod (#14) position.

Figure 5:
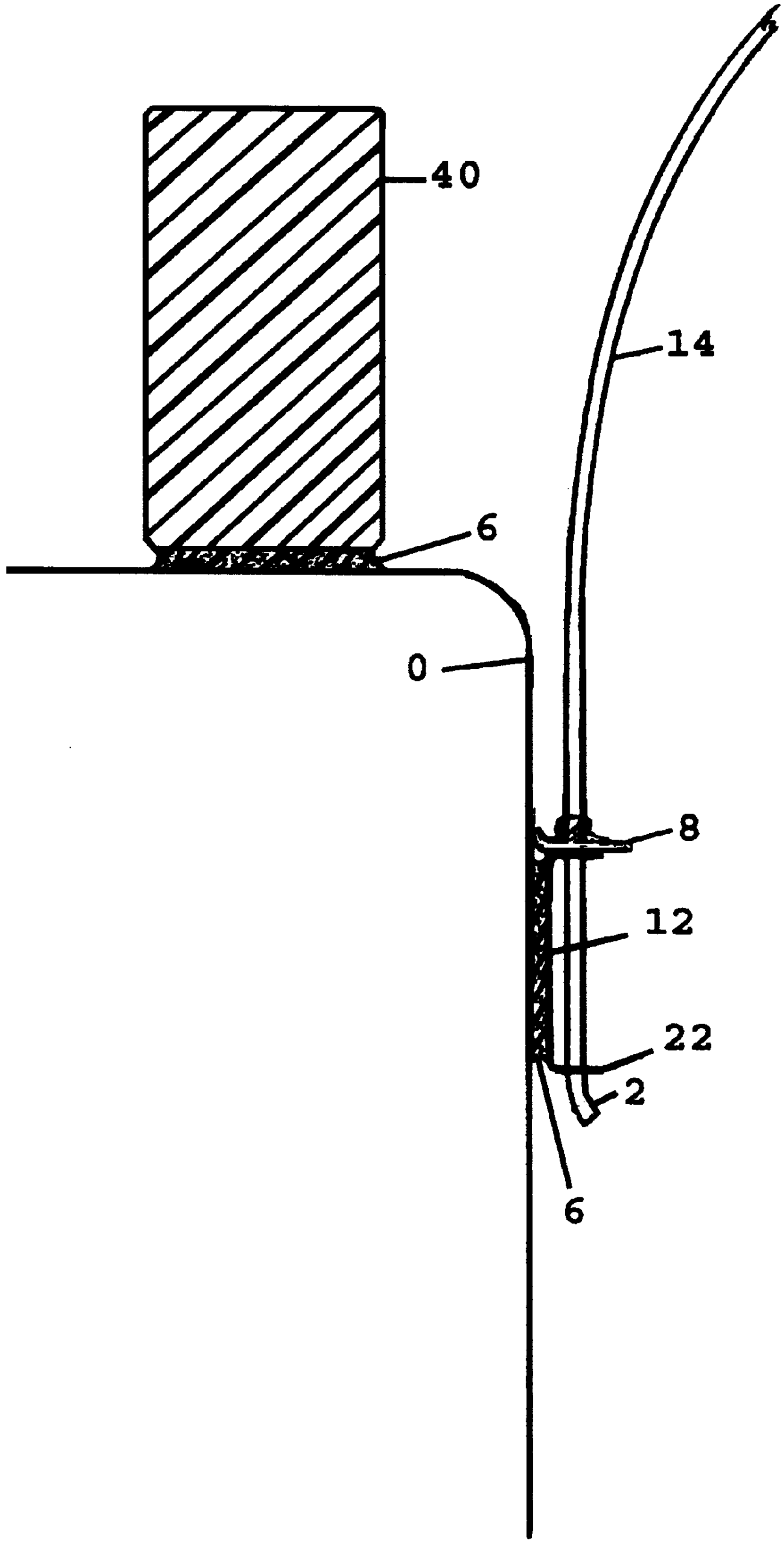

FIG. 5 is a perspective drawing of a computer monitor chassis (#0) with Micro Fan (#40) and attached bracket (#12) with partial connecter rod(#14) leading to the device.

Figure 6:
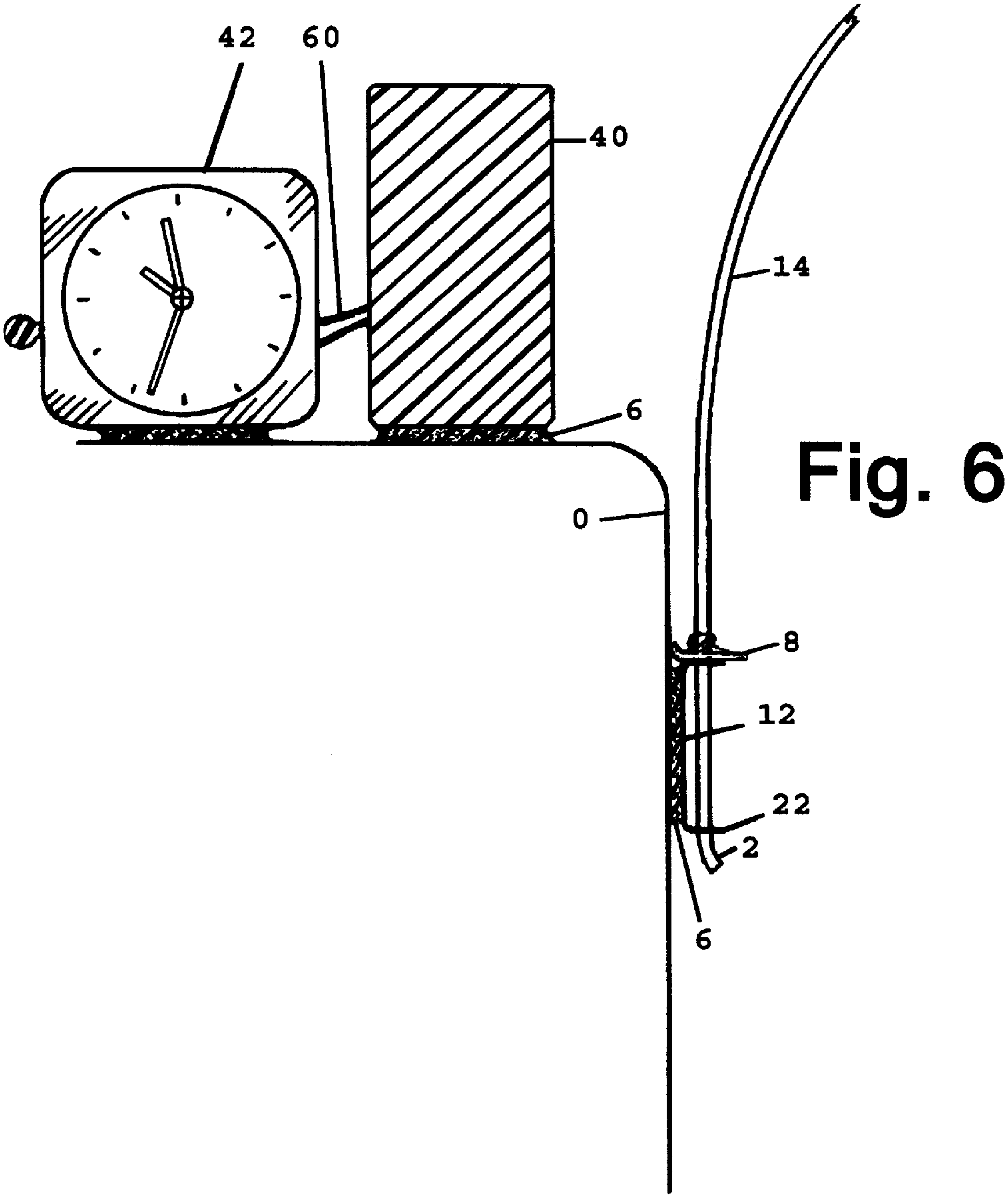

FIG. 6 is a perspective drawing of a computer monitor chassis (#0) with Micro Fan (#40) and clock timer (#42)and attached bracket(#12) with partial connector rod (#14) leading to the device.

Figure 7:
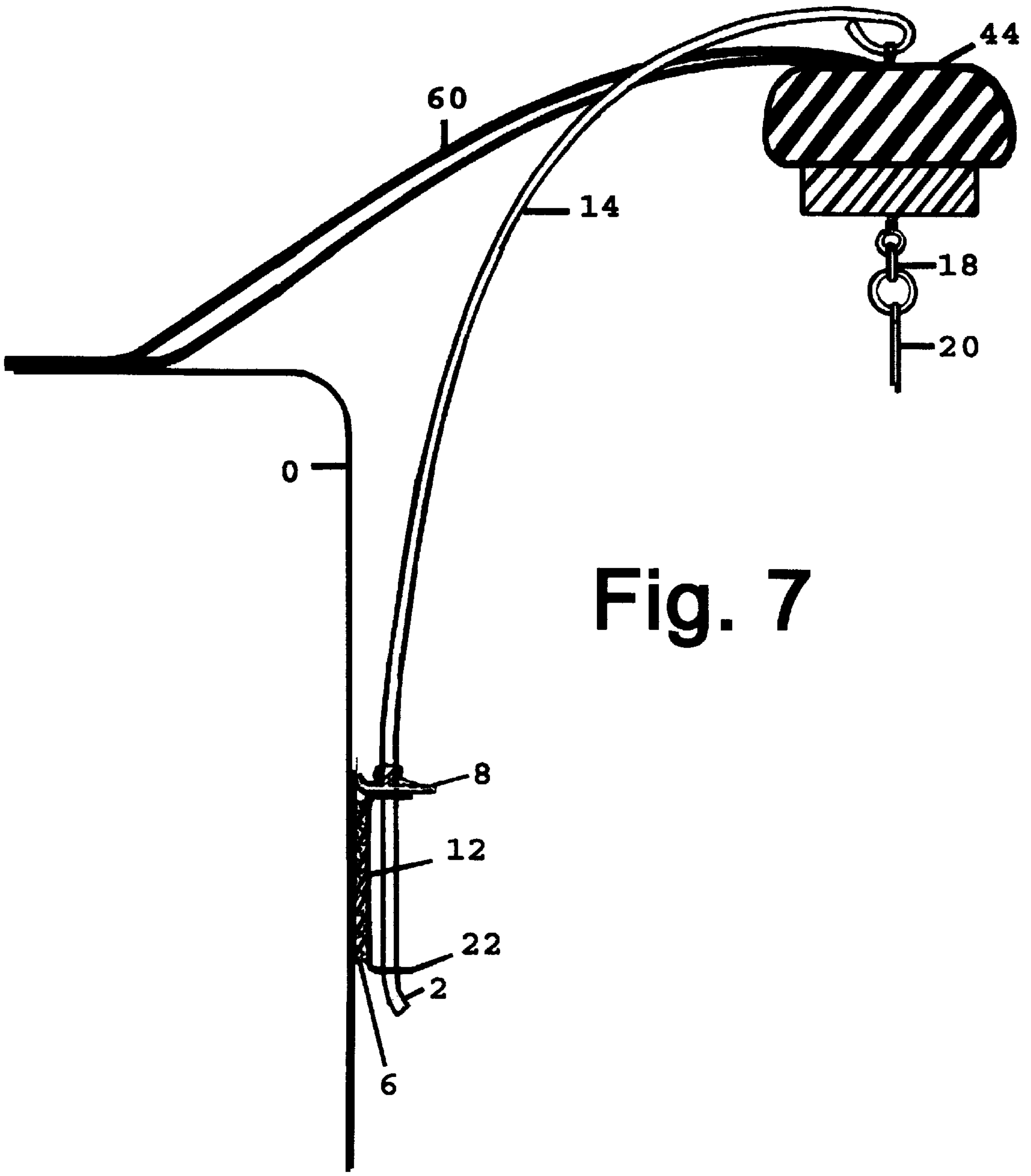

FIG. 7 is a perspective drawing of a computer monitor chassis (#0) with the attached bracket (#12), connecting rod (#14), motor (#44), jump ring connector (#18) and partial wireform (#20) leading to invention.

Figure 8:
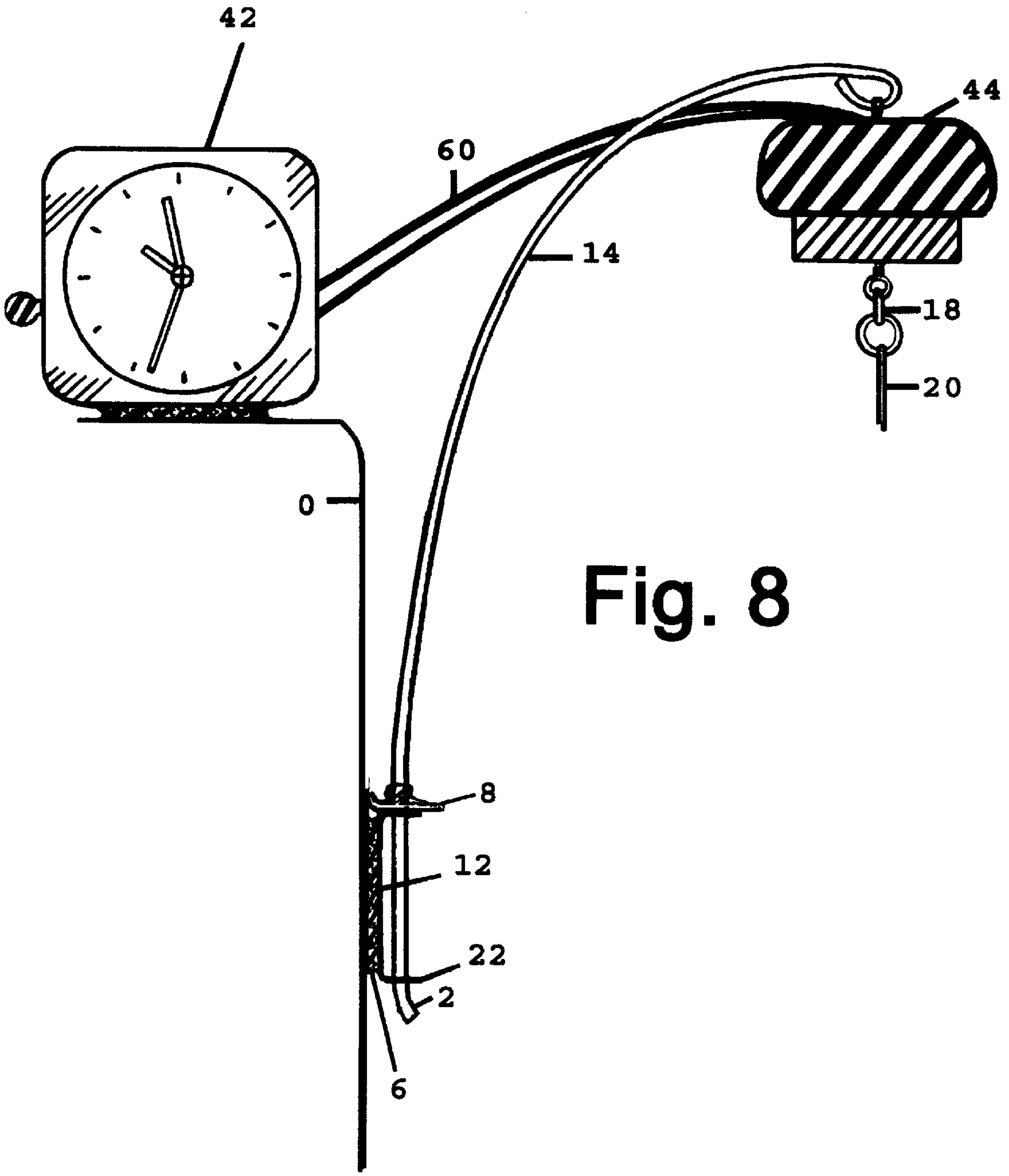

FIG. 8 is a perspective drawing of a computer monitor chassis (#0) with clock timing mechanism to activate motor (#46),the attached bracket (#12), connecting rod (#14), motor (#44), jump ring connector (#18) and partial wireform (#20) leading to invention.

Figure 9:
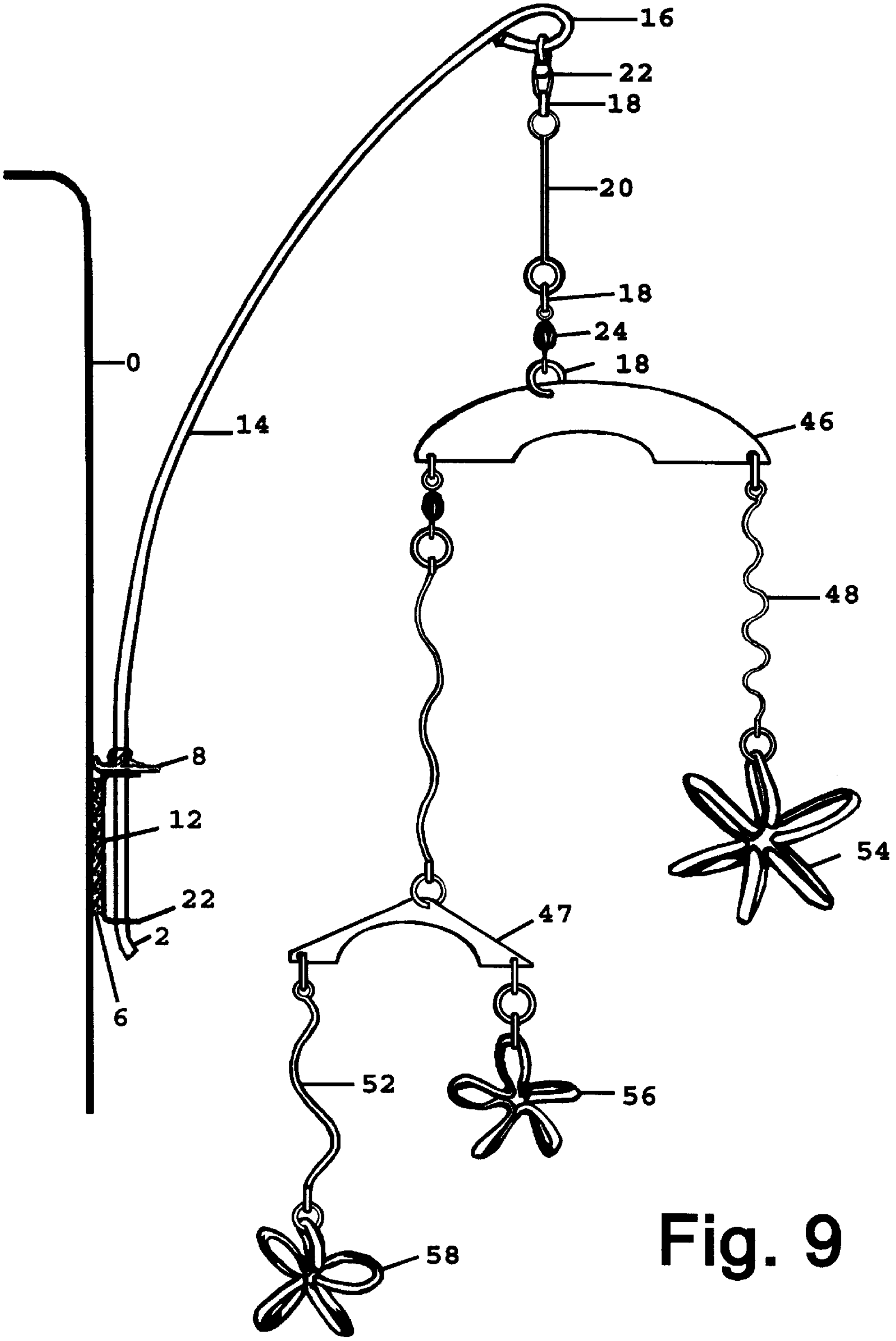

FIG. 9 is a perspective drawing of an alternative embodiment of said device with bracket (#12) connector rod (#14) spring clip (#22) and associated wireforms (#20), jumprings (#18), spinners(#24), balancing elements (#46, #48), wireforms (#48, #50, #52), and distal visual units (#54, #56, #58) with all connections thereto.

What is claimed is:

1. A method of stimulating and exercising the eye muscles with a mechanical device having one or more visual elements rotationally suspended from a supporting rod, said supporting rod rotationally connected to a connector having a generally flat surface, the surface containing a means for connecting to an opposite flat surface on a computer monitor, the method comprising the steps of:

A. mounting said device on a monitor by attaching the flat surface of the connector to a flat surface on the monitor;

B. moving said visual elements about said supporting rod.

2. The method of claim 1 wherein a timing mechanism periodically moves the visual elements.

3. The method of claim 2 wherein the movement is actuated by a motorized micro-fan.

4. The method of claim 3 wherein the timing mechanism periodically actuates the micro-fan.

5. The method of claim 1, wherein said mechanical device has five visual elements.

6. A device for stimulating and exercising eye muscles of a viewer of a computer monitor, the device comprised of:

a supporting rod with a first end and a second end;

means for connecting the first end of the supporting rod to the computer monitor; and;

visual elements rotationally suspended from the second end of the supporting rod.

7. The device of claim 6 wherein the means for connecting the first end of the supporting rod to the computer monitor comprises a plate which is capable of being adhered to a flat surface of the computer monitor.

8. The device of claim 7 wherein the first end of the supporting rod is pivotally connected to the flat plate.

9. The device of claim 6 wherein the visual elements include a first balancing element with two ends, one end connected to a first distal visual unit and the second end connected to a second distal balancing element.

10. The device of claim 9 wherein the second distal balancing element has two ends, each end being connected to a distal visual element.

11. The device of claim 9 wherein the supporting rod is connected to the first balancing element by a wire form.

* * * * *